United States Patent [19]

Fischer et al.

[11] Patent Number: 4,480,123
[45] Date of Patent: Oct. 30, 1984

[54] PREPARATION OF DIACYLOXYALKADIENES

[75] Inventors: Rolf Fischer, Heidelberg; Hans-Martin Weitz, Bad Dürkheim, both of Fed. Rep. of Germany

[73] Assignee: BASF Aktiengesellschaft, Ludwigshafen, Fed. Rep. of Germany

[21] Appl. No.: 516,979

[22] Filed: Jul. 25, 1983

Related U.S. Application Data

[62] Division of Ser. No. 330,091, Dec. 14, 1981.

[30] Foreign Application Priority Data

Jan. 15, 1981 [DE] Fed. Rep. of Germany ....... 3101002

[51] Int. Cl.³ ............................................ C07C 67/055
[52] U.S. Cl. ..................................... 560/244; 560/262; 568/852; 568/857; 568/858
[58] Field of Search ......................................... 560/244

[56] References Cited

U.S. PATENT DOCUMENTS

| | | | |
|---|---|---|---|
| 3,755,423 | 8/1973 | Onoda | 560/244 |
| 3,872,163 | 3/1975 | Shimizu | 560/244 |
| 3,922,300 | 11/1975 | Onoda | 560/244 |
| 4,121,039 | 10/1978 | Parthasarthy | 560/244 |
| 4,131,743 | 12/1978 | Yoshida | 560/244 |
| 4,225,727 | 9/1980 | Kamiyama | 560/244 |
| 4,233,455 | 11/1980 | Weitz | 560/244 |

*Primary Examiner*—Michael L. Shippen
*Attorney, Agent, or Firm*—John H. Shurtleff

[57] ABSTRACT

A process for preparing diacyloxyalkadienes of the formula

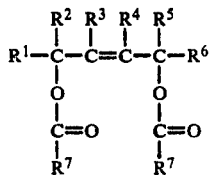

where $R^1$ to $R^6$ are each hydrogen or a hydrocarbon radical, which contain one or more hydrocarbon radicals having one or more non-conjugated double bonds, by reacting an aliphatic triene of the formula

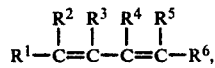

in which $R^1$ to $R^6$ have the same meanings given above with a carboxylic acid of the formula

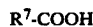

in which $R^7$ has the same meaning given above, in the presence of a catalyst which contains palladium, platinum or salts of these metals and in the presence of oxygen.

13 Claims, No Drawings

PREPARATION OF DIACYLOXYALKADIENES

This is a division of application Ser. No. 330,091 filed Dec. 14, 1981.

The present invention relates to novel diacyloxyalkadienes which contain two or more mutually non-conjugated double bonds and whose acyloxy groups are located in positions 1 and 4 with respect to each other, and to a process for their preparation by the reaction of aliphatic trienes, containing two mutually conjugated and one or more isolated double bonds, with carboxylic acids and oxygen in the presence of catalysts.

The novel diacyloxyalkadienes have the general formula

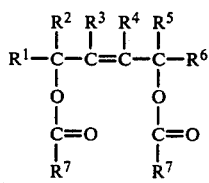    I where $R^1$ to $R^5$ are each hydrogen or a hydrocarbon radical of 1 to 6 carbon atoms, $R^6$ is hydrogen or a hydrocarbon radical of 3 to 9 carbon atoms having one or more non-conjugated double bonds, and $R^7$ is hydrogen or alkyl of 1 to 5 carbon atoms, and in the case in which $R^6$ is hydrogen, one or more of $R^1$ to $R^5$ are $R^8-CH_2-$, where $R^8$ is a hydrocarbon radical of 2 to 5 carbon atoms which contains one or more non-conjugated double bonds.

$R^1$ to $R^5$ can each be hydrogen or a hydrocarbon radical of 1 to 6 carbon atoms. The hydrocarbon radicals are preferably straight-chain radicals and can also contain double bonds which, however, are conjugated neither with one another nor with the double bonds in the starting compounds of the formula II. Examples of hydrocarbon radicals of this type are alkyl, alkenyl or alkadienyl, eg. $CH_3-$, $C_2H_5-$, $C_3H_7-$, n—$C_4H_9-$, sec.-butyl, i-butyl, tert.-butyl, $CH_2=CH-$, $CH_3-CH=CH-$, $CH_3-CH=CH-CH_2$, $CH_3-C(CH_3)=CH-$, $CH_3-C(CH_3)=CH-CH_2-$, $CH_3-C(CH_3)=CH-CH_2-CH_2-$, $CH_2=CH-CH_2-$, $CH_2=C(CH_3)-CH_2-$, $CH_2=CH-C(CH_3)-$, $CH_2=CH-CH_2-CH_2-$, $CH_2=CH-CH_2-CH=CH-$ or $CH_2=CH-CH_2-CH=CH-CH_2-$.

The hydrocarbon radicals $R^6$ are of 3 to 9 carbon atoms, with one or more non-conjugated double bonds, examples being $-CH_2-C(CH_3)=CH_2$, $-CH_2-CH_2-C(CH_3)=CH_2$, $-CH_2-CH_2-CH=CH_2$, $-CH_2-C(CH_3)=CH-CH_3$, $-CH_2-CH=CH_2$, $-CH_2-C(CH_3)=CH_2$, $-CH_2-CH=CH-CH_3$, $-CH_2-CH=C(CH_3)_2$, $-CH_2-CH=CH-CH_2-CH=CH_2$, $-CH_2-CH=CH-(CH_2)_2-CH=CH_2$ or $-CH_2-CH=CH-(CH_2)_4-CH=CH_2$.

Methyl, ethyl, propyl and butyl are examples of suitable alkyl $R^7$.

Of particular industrial interest are the diacyloxydialkadienes of the formula I which contain, in total, two or three non-conjugated double bonds and in which $R^7$ is hydrogen or alkyl of 1 to 3 carbon atoms.

The novel diacyloxyalkadienes of the formula I are obtained when an aliphatic triene of the formula

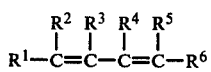    II where $R^1$ to $R^6$ have the above meanings, is treated with a carboxylic acid of the formula $R^7$—COOH, where $R^7$ has the above meaning, in the presence of catalysts containing palladium, platinum or salts of these metals and in the presence of oxygen.

Where 1,3,7-octatriene is reacted with oxygen and acetic acid, the reaction can be represented by the following equation:

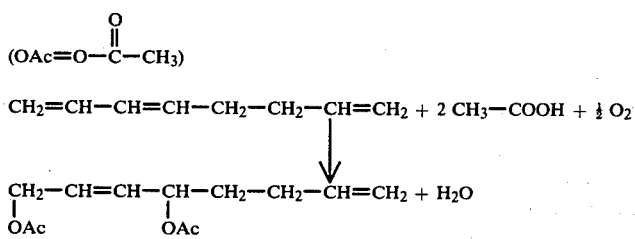

It is known that 1,3-butadiene, which may be substituted by alkyl or acyloxy, can be reacted with oxygen and carboxylic acids, in the presence of catalysts containing palladium or platinum, to give but-2-ene-1,4-diol diesters and but-1-ene-3,4-diol diesters. Catalysts in homogeneous solution or supported catalysts can be used for this purpose. For example, according to British Patent No. 1,138,366, mixtures of 1,4-diacetoxybut-2-ene and 3,4-diacetoxybut-1-ene in the molar ratio of 1:1 are obtained by the reaction of butadiene with acetic acid in the presence of palladium chloride, copper acetate and lithium acetate. According to British Patent No. 1,277,837, 1,3-butadiene is reacted in a similar manner with oxygen, in the presence of potassium acetate, copper acetate and palladium acetate dissolved in glacial acetic acid, to give 1,4-diacetoxybut-2-ene.

German Patent No. 2,217,452 describes a process for the acetoxylation of butadiene, in which process the supported palladium catalysts used contain, in addition, antimony, bismuth, tellurium or selenium. According to German Laid-Open application DOS No. 2,820,519, supported catalysts are used which contain palladium and copper in the form of an intermetallic compound. German Laid-Open application DOS No. 2,417,558 describes supported platinum catalysts which additionally contain one of the elements phosphorus, arsenic, antimony, selenium or tellurium. In the reaction of butadiene with oxygen and acetic acid (acetoxylation), cis- and trans-but-1-ene-1,4-diol diacetates are very predominantly formed in the presence of the stated catalysts, but-1-ene-3,4-diol monoacetate and but-1-ene-3,4-diol diacetate being formed in minor quantities.

Furthermore, it is known that the reaction of ethylene in the presence of palladium acetate, copper chloride, alkali metal acetates and acetic acid yields mixtures of 1,2-diacetoxyethane, 1-hydroxy-2-acetoxyethane and 1-chloro-2-acetoxyethane (P. M. Henry, J. Org. Chem. 32 (1967), 2,575).

On the basis of the prior art, it was to be expected that, in the novel process, an addition of acyloxy groups at the isolated double bonds would also occur. The fact that this is not the case is surprising. The process according to the invention also yields the novel diacyloxyalkadienes by a particularly advantageous route. A possible alternative, namely the conventional addition reaction of bromine with 1,3-dienes, such as isoprene, and the subsequent reaction of 1,4-dibromo-2-alkenes with alkali metal acetates to prepare the 1,4-diacetoxy compound (A. F. Shepard, J. R. Johnson, J. Amer. Chem. Soc. 54 (1932), 4,388) would lead to the addition of bromine at the isolated double bond when the method is applied to the trienes of the formula II.

Examples of trienes which are suitable as starting materials of the formula II are 1,3,6-octatriene, 1,3,7-octatriene, 2,6-dimethyl-1,3,7-octatriene, 2,7-dimethyl-1,3,7-octatriene, 3,7-dimethyl-1,3,6-octatriene (ocimene), myrcene, 1,3,6,10-dodecatetraene and 1,5,7,10,15-hexadecapentaene. The olefins of the formula II can be used individually or as mixtures which, for examples, can also contain other hydrocarbons, such as monoolefins and paraffins.

The starting compounds mentioned can be prepared, for example, by dimerization and trimerization of 1,3-dienes. Thus, 1,3,6-octatriene and 1,3,7-octatriene are obtainable by dimerization of butadiene in the presence of nickel catalysts (German Laid-Open application DOS No. 1,443,442), 2,6-dimethyl-1,3,7-octatriene and 2,7-dimethyl-1,3,7-octatriene are obtainable by dimerization of isoprene in the presence of palladium compounds (H. Yagi et al., Synthesis 1977, 334), 1,3,6,10-dodecatetraene is obtainable by trimerization of butadiene (D. Medima, R. van Helden, Rec. Trav. Chim. 90 (1971), 324) and 1,5,7,10,15-hexadecapentaene is obtainable by dimerization of 1,3,7-octatriene (W. Keim, and H. Chung, J. Org. Chem. 37 (1972), 947).

Formic acid, acetic acid, propionic acid, butyric acid and valeric acid are examples of suitable carboxylic acids.

Palladium, platinum or salts of these metals are used as catalysts, which can also contain other active constituents. Examples of suitable supported catalysts are those which contain palladium or platinum and copper and/or tellurium as active constituents, applied to the carrier. The catalysts can be prepared in a conventional manner, for example according to German Patent No. 2,217,452 and German Laid-Open applications DOS Nos. 2,820,519, DOS 2,417,452, DOS 2,820,519 and DOS 2,417,558, and contain, for example, from 1 to 10% of palladium or platinum, from 0.1 to 30% of copper and/or from 0.01 to 10% of tellurium, based on the weight of the catalyst. The supported catalyst preferably used contains, per gram atom of palladium or platinum, from 0.01 to 6, preferably from 1 to 3.5; gram atoms of copper and/or from 0.01 to 0.4, gram atom of tellurium.

The total quantity of catalytically active metals applied to the support is advantageously, for example, from 0.01 to 30% by weight, based on the supported catalyst, but it is also possible to use higher or lower concentrations. Examples of carriers for the catalysts are active charcoal, bauxite, pumice, silica gel, kieselguhr or other forms of silica, magnesium oxide, clay and aluminum oxide.

The catalytically active metals can, for example, also be used without a carrier, by dissolving or suspending the catalyst, in the form of a salt, in the reaction mixture.

The reaction for the preparation of diacyloxyalkadienes is carried out, in a conventional manner, in the gas or liquid phase at from 70° to 180° C. In the gas phase, the reaction is preferably carried out at from 120° to 150° C., and in the liquid phase preferably at from 70° to 110° C. The reaction pressure is determined by the procedure and can be from atmospheric pressure to, for example, 100 bar. The process can be carried out batchwise or continuously, for example in a fixed bed, fluidized bed or three-phase fluidized bed. Unreacted trienes II can be distilled off, together with the particular carboxylic acid, from the reaction mixture after the reaction and can be re-used in the form of this distillate.

The novel diacyloxyalkadienes of the formula I are valuable intermediates which, after hydrogenation and hydrolysis, give substituted 1,4-diols which can, like 1,4-butanediol, 1,6-hexanediol (Ullmanns Encyklopädie, Volume 7, page 228) and 1,8-octanediol (German Laid-Open application DOS No. 1,066,566), be used for the preparation of polyurethanes, esters and plasticizers. Diacyloxyalkadienes of the formula I in which $R^1$, $R^2$, $R^4$ and $R^5$ are hydrogen, $R^3$ and $R^6$ to $R^8$ are alkyl or alkenyl and $R^9$ is alkyl can be reacted with water, in the presence of a cation exchanger or mineral acid, to give $\alpha,\beta$-unsaturated aldehydes.

EXAMPLE 1

(a) Catalyst Preparation 89.6 g of copper powder are dissolved in 660 cm³ of 33% strength nitric acid, and this solution is mixed, at room temperature, with a solution of 83.4 g of PdCl₂ in 400 cm³ of a warm mixture of equal volumes of 66% strength nitric acid and 32% strength hydrochloric acid and with a solution of 6.25 g of TeO₂ in 1,000 cm³ of warm 16% strength hydrochloric acid. The combined metal salt solution is added to 1,000 g of active charcoal (0.3 to 0.5 mm) which has beforehand been stirred with 15% strength nitric acid at 70° for 5 hours, filtered off under suction, washed until neutral and dried at 150° C. under reduced pressure. A quantity of water sufficient to completely wet the charcoal is then added.

The mixture is then evaporated to dryness in a rotary evaporator at 85° C. under reduced pressure from a water pump. The catalyst is dried in a drying oven under reduced pressure for 2 hours at 150° C. and then under a stream of nitrogen in a tube oven for 2 hours at 150° C. Thereafter the catalyst is activated by passing over it, at 400° C., nitrogen saturated at room temperature with methanol, followed finally by 20 l/hour of hydrogen for 30 minutes at 800° C. The catalyst is allowed to cool to room temperature under a stream of nitrogen.

According to elementary analysis, the catalyst contains 5.24% of palladium, 8.8% of copper and 0.53% of tellurium.

(b) Preparation of 1,4-diacetoxy-2,7-octadiene by acetoxylation of 1,3,7-octatriene An apparatus comprising a 1 liter three-necked flask equipped with an Anschütz head, a dropping funnel, a gassing stirrer, an internal thermometer, a gas inlet tube and a reflux condenser surmounted by a dry ice condenser is flushed with nitrogen. A suspension of 25 g of the catalyst, prepared according to Example (1a), in 543 g of glacial acetic acid is then introduced into the apparatus. It is heated to 95° C. and 12 l of oxygen are introduced in the course of 4 hours, with simultaneous dropwise addition of 54 g of 1,3,7-octatriene. A total of 1.5 l of oxygen is then introduced for a further 30 minutes at 95° C., after which the apparatus is flushed with nitrogen for 30 minutes. The mixture is allowed to cool and the catalyst is removed by filtration. The resulting 598 g of acetic acid solution are evaporated down in a rotary evaporator. Fractional distillation of the residue gives 37 g of unreacted 1,3,7-octatriene, corresponding to a 32% conversion, and 23.1 g of 1,4-diacetoxy-2,7-octadiene (65%, based on 1,3,7-octatriene converted), of boiling point 101° to 106° C./0.7 mbar and $n_D^{20} = 1.4539$.

EXAMPLE 2

Preparation of 2,7-dimethyl-1,4-diacetoxy-2,7-octadiene by acetoxylation of 2,7-dimethyl-1,3,7-octatriene The procedure described in Example (1b) is followed, but a suspension of 12.5 g of a catalyst, prepared according to German Laid-Open application DOS No. 2,820,519 and containing 5.27% of Pd and 8.59% of Cu on an active charcoal carrier, in 500 g of acetic acid is introduced into the apparatus. In the course of 2 hours at 95° C., 6 l of oxygen are introduced and 34 g of 2,7-dimethyl-1,3,7-octatriene are added dropwise. A total of 1.5 l of oxygen is then introduced for a further 30 minutes at 95° C., after which the apparatus is flushed with nitrogen for 30 minutes. Working-up as described in Example 1b and fractional distillation of the acetic acid solution yield 11 g of 2,7-dimethyl-1,4-diacetoxy-2,7-octadiene of boiling point 113° to 115° C./1.2 mbar and $n_D^{20} = 1.4625$, and 25 g of unreacted 2,7-dimethyl-1,3,7-octatriene, corresponding to a conversion of 26%.

EXAMPLE 3

Preparation of 2,6-dimethyl-1,4-diacetoxy-2,7-octadiene by acetoxylation of 2,6-dimethyl-1,3,7-octatriene:

In the manner described in Example (1b), 6 l of oxygen are introduced and 34 g of 2,6-dimethyl-1,3,7-octatriene are added dropwise, in the course of 2 hours at 95° C., to a suspension of 12.5 g of a catalyst, prepared according to German Laid-Open application DOS No. 2,217,452 and containing 5.1% of Pd and 0.9% of Te on an active charcoal carrier, in 540 g of acetic acid. A total of 1.5 l of oxygen is then introduced for a further 30 minutes at 95° C., after which the apparatus is flushed with nitrogen for 30 minutes. Working-up and distillation yield 15.2 g of 2,6-dimethyl-1,4-diacetoxy-2,7-octadiene of boiling point 94° to 98° C./0.8 mbar and $n_D^{20} = 1.4576$, and 21 g of unreacted 2,6-dimethyl-1,3,7-octatriene, corresponding to a conversion of 38%.

EXAMPLE 4

In the manner described in Example (1b), 12 l of oxygen are introduced and 50 g of 7-methyl-3-methylene-1,6-octadiene (myrcene) are added dropwise, in the course of 4 hours at 95° C., to a suspension of 25 g of a catalyst, prepared according to Example (1a) and containing 5.04% of Pd, 8.2% of Cu and 0.55% of Te on an active charcoal carrier, in 543 g of acetic acid. A total of 1.5 l of oxygen is then introduced for a further 30 minutes at 95° C., after which the apparatus is flushed with nitrogen for 30 minutes. Working-up as described in Example (1b) and fractional distillation of the acetic acid solution yield 37 g of 2-(4-methyl-3-pentenyl)-1,4-diacetoxy-but-2-ene of boiling point 112° to 119° C./0.5 mbar and $n_D^{20} = 1.4678$, and 18 g of unreacted 7-methyl-3-methylene-1,6-octadiene, corresponding to a conversion of 64%.

We claim:

1. A process for the preparation of a diacyloxyalkadiene of the formula

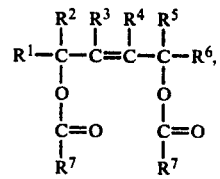

where $R^1$ to $R^5$ are each hydrogen or a hydrocarbon radical of 1 to 6 carbon atoms, $R^6$ is hydrogen or a hydrocarbon radical of 3 to 9 carbon atoms having one or more non-conjugated double bonds, and $R^7$ is hydrogen or alkyl of 1 to 5 carbon atoms, and in the case in which $R^6$ is hydrogen, one or more of $R^1$ to $R^5$ are $R^8$—$CH_2$— where $R^8$ is a hydrocarbon radical of 2 to 5 carbon atoms having one or more non-conjugated double bonds, which process comprises:

reacting an aliphatic triene of the formula

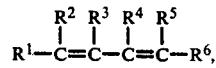

where $R^1$ to $R^6$ have the meanings given above, with a carboxylic acid of the formula

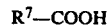

where $R^7$ has the meaning given above, and with oxygen at an elevated temperature in the presence of a catalyst which contains palladium, platinum or salts of these metals.

2. A process as claimed in claim 1 wherein the initial reactant II and the final product I each contain two or three non-conjugated double bonds and $R^7$ is hydrogen or alkyl of 1 to 3 carbon atoms.

3. A process as claimed in claim 1 wherein the catalyst contains, as active components, platinum or palladium and at least one metal selected from the group consisting of copper and tellurium.

4. A process as claimed in claim 3 wherein the active catalyst components consist essentially of from 1 to 10% by weight of platinum or palladium, up to 30% by weight of copper and up to 10% by weight of tellurium, based on the catalyst weight.

5. A process as claimed in claim 3 wherein the active catalyst components are applied to a carrier to provide a supported catalyst.

6. A process a claimed in claim 5 wherein the total quantity of the catalytically active metals applied to the carrier is about 0.01 to 30% by weight, based on the supported catalyst.

7. A process as claimed in claim 6 wherein the supported catalyst contains up to 6 gram atoms of copper and up to 1 gram atom of tellurium per gram atom of platinum or palladium.

8. A process as claimed in claim 1 wherein the reaction is carried out in the liquid or gas phase at about 70° to 180° C.

9. A process as claimed in claim 3 wherein the reaction is carried out in the liquid phase at about 70° to 110° C.

10. A process as claimed in claim 3 wherein the reaction is carried out in the gas phase at about 120° to 150° C.

11. A process as claimed in claim 7 wherein the supported catalyst contains, per gram atom of platinum or palladium, from 1 to 3.5 gram atoms of copper and/or from 0.01 to 1 gram atoms of tellurium.

12. A process as claimed in claim 7 carried out in the liquid or gas phase at a temperature of about 70° to 180° C.

13. A process as claimed in claim 12 wherein the supported catalyst contains, per gram atom of platinum or palladium, from 1 to 3.5 gram atoms of copper and/or from 0.01 to 1 gram atom of tellurium.

* * * * *